United States Patent [19]

Abou-Gharbia

[11] Patent Number: 4,748,247

[45] Date of Patent: May 31, 1988

[54] 2-[4-[4-(2-PYRIMIDINYL)-1-PIPERAZINYL-]ALKYL]ALKYL]PYRIDO- AND PYRAZINO-INDOLE-1,3-DIONE DERIVATIVES AS HISTAMINE $H_1$ ANTAGONISTS

[75] Inventor: Magid A. Abou-Gharbia, Wilmington, Del.

[73] Assignee: American Home Products Corporation, New York, N.Y.

[21] Appl. No.: 921,642

[22] Filed: Oct. 21, 1986

[51] Int. Cl.[4] ............... C07D 403/14; A61K 31/495
[52] U.S. Cl. .................................. 544/357; 544/331; 544/359; 544/360; 544/361; 544/372; 544/405; 544/408; 546/86; 546/87; 548/300; 548/428; 548/429
[58] Field of Search ............... 544/357, 359, 360, 372, 544/331, 405, 408, 361; 548/300, 428, 429; 546/86, 87; 514/253, 256, 292, 333, 385, 252

[56] References Cited

U.S. PATENT DOCUMENTS

| 3,522,262 | 7/1970 | Berger | 546/86 |
| 4,153,711 | 5/1979 | Zinnes et al. | 548/429 |
| 4,252,811 | 2/1981 | Welch et al. | 546/86 |
| 4,478,750 | 10/1984 | Gadient | 546/86 |

Primary Examiner—Donald G. Daus
Assistant Examiner—Cecilia Shen
Attorney, Agent, or Firm—Richard K. Jackson

[57] ABSTRACT

Histamine $H_1$ receptor antagonists of the formula:

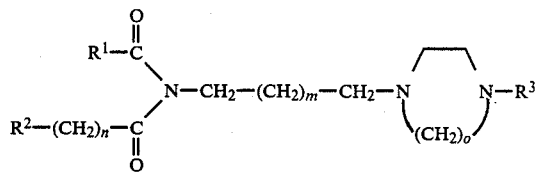

in which
$R^1$ and $R^2$ taken together represent an ortho-fused 1,2-indolo or 2,3-indolo moiety of the formulas:

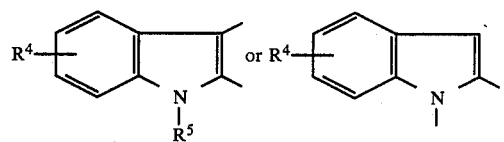

where
$R^4$ is hydrogen, alkyl of 1 to 6 carbon atoms, alkoxy of 1 to 6 carbon atoms or halo; and
$R^5$ is hydrogen, alkyl of 1 to 6 carbon atoms, benzyl, phenyl or substituted phenyl or benzyl where the substituent is taken from the group alkyl of 1 to 6 carbon atoms, alkoxy of 1 to 6 carbon atoms, halo or trifluoromethyl;
$R^3$ is

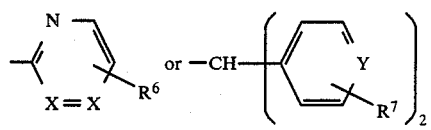

where
one X is —N= and the other is —CH=;
Y is —N= or —CH=;
and $R^6$ and $R^7$ are alkyl of 1 to 6 carbon atoms, alkoxy of 1 to 6 carbon atoms or halo;
n is one of the integers 0 or 1;
m is one of the integers 0, 1, 2 or 3; and
o is one of the integers 1 or 2;
or a pharmaceutically acceptable salt thereof.

5 Claims, No Drawings

2-[4-[4-(2-PYRIMIDINYL)-1-PIPERAZINYL]ALK-YL]ALKYL]PYRIDO- AND PYRAZINO-INDOLE-1,3-DIONE DERIVATIVES AS HISTAMINE H₁ ANTAGONISTS

DESCRIPTION OF THE INVENTION

In accordance with this invention, there is provided a group of histamine $H_1$ receptor antagonists of the formula:

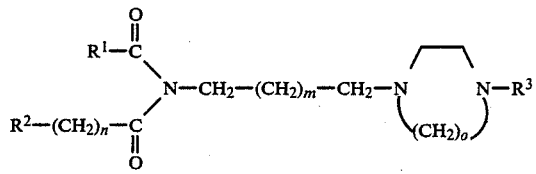

in which
$R^1$ and $R^2$ taken together represent an ortho-fused 1,2-indolo or 2,3-indolo moiety of the formulas:

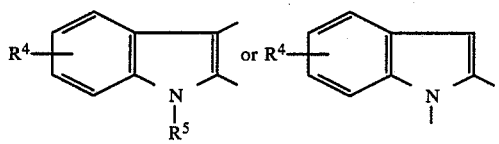

where
$R^4$ is hydrogen, alkyl of 1 to 6 carbon atoms, alkoxy of 1 to 6 carbon atoms or halo; and
$R^5$ is hydrogen, alkyl of 1 to 6 carbon atoms, benzyl, phenyl or substituted phenyl or benzyl where the substituent is taken from the group alkyl of 1 to 6 carbon atoms, alkoxy of 1 to 6 carbon atoms, halo or trifluoromethyl;
$R^3$ l is

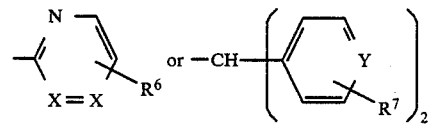

where
one X is —N= and the other is —CH=;
Y is —N= or —CH=;
and $R^6$ and $R^7$ are alkyl of 1 to 6 carbon atoms, alkoxy of 1 to 6 carbon atoms or halo;
n is one of the integers 0 or 1;
m is one of the integers 0, 1, 2 or 3; and
o is one of the integers 1 or 2;
or a pharmaceutically acceptable salt thereof.

The preferred histamine $H_1$ receptor antagonists are those of the formula:

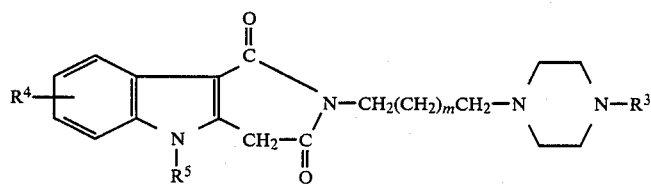

in which the variable m and radicals $R^3$, $R^4$ and $R^5$ are described above, or a pharmaceutically acceptable salt thereof.

The pharmaceutically acceptable salts are prepared conventionally with organic or inorganic acids such as hydrochloric, hydrobromic, sulfuric, phosphoric, nitric, acetic, fumaric, citric, tartaric, maleic, lactic, 2-hydroxyethanesulfonic, methanesulfonic, toluene-4-sulfonic, ethanesulfonic acid, and the like.

The compounds of this invention are prepared by reaction of an appropriately substituted 3-carb(lower)alkoxymethyl indole-2-acetic acid loweralkyl ester or an appropriately substituted 1-carb(lower)alkoxymethyl-2-acetic acid lower alkyl ester with

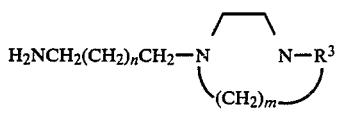

to produce an indole acetic acid amide-ester which is ring-closed with alcoholic sodium alkoxide at reflux temperatures. The intermediate reactants employed in production of the compounds of this invention are either known compounds or are readily prepared by methods known in the art.

The histamine $H_1$ receptor antagonist activity of the compounds of this invention was established by subjecting them to the following standard test procedures for $H_1$-blocking activity:

Fresh segments of terminal ileum immediately proximal to Peyer's patch, otained from male Buckshire guinea pigs, were suspended in 37° C. Tyrode's solution in a tissue bath and aerated. The tissue segments were placed under one gram tension and allowed to equilibrate for one hour. Histamine was added to each tissue bath to a final concentration of $1 \times 10^{-6}M$. The contraction response after it equilibrated was noted as grams tension. Test drug was added, in the presence of histamine, to each bath to a final concentration of $1 \times 10^{-7}M$. The change in grams tension was noted and the percent reduction in grams tension calculated.

Following this procedure, with quadruplicate sets of tissues, the compound of Example 1 demonstrated 11 percent reduction in tissue contraction and the compounds of Examples 2 and 3 provided 41 and 17 percent reduction in contraction, respectively.

The pharmacological results obtained characterize the compounds of this invention as $H_1$-receptor antagonists useful in the treatment of mammals experiencing conditions such as asthma, hay fever, allergic rhinitis, atopic dermatitis, conjunctivitis, pruritis, and eczema, or other responses where histamine is released and acts on $H_1$ receptors. As such, they may be administered topically or systemically. Topical administration is advantageously achieved to the skin via creams, ointments or lotions, or via aerosol introduction into the respiratory tract. Systemic administration may be orally, nasally, infrabronchially, parenterally or rectally. In each instance, conventional formulations amenable to use in the desired administration route are appropriate. Hence, tablets and capsules may be prepared for oral administration, suppositories for rectal administration, isotonic aqueous solutions for intravenous, subcutaneous or intramuscular injection and aerosol suspensions for inhalation.

As is conventional in the use of antihistamine agents, the appropriate dosage is determined on a subjective basis by initial administration of small amounts, ca. 0.5-15 mg. followed by increasing quantities up to about 400 mg., depending upon the desired route of administration, until the desired symptomatic relief is obtained. The dosage is personalized in this manner for each patient, based upon size, age, type of discomfort, degree of disability, etc., by the physician.

The following examples illustrate the preparation of representative compounds of the invention.

EXAMPLE 1

4,5-Dihydro-5-methyl-2-[4-[4-(2-pyridmidinyl)-1-piperazinyl]butyl]1H-pyrido[4,3-b]indole-1,3(2H)-dione A suspension 3-carbethoxy-1-methylindole-2-acetic acid ethyl ester (Ali et al., Z. Natur forsch., 316, 589-593 (1976) 5.7 g (0.01 mole) and 1-(4-aminobutyl)-4-(2-pyrimidinyl)piperazine 4.7 g (0.01 mole) were heated in an oil bath at 130° C. for 18 hours. The reaction mixture was cooled and the semisolid residue was triturated with ethyl alcohol to afford a buff precipitate which was filtered and dried to afford 3 g (58.8% yield) of the corresponding amide ester intermediate, mp 138°-139° C.

The title compound was prepared by dissolving 3 g of the amide ester intermediate in 30 ml of boiling ethanol. To the refluxed solution, 0.23 g (0.01 equivalent) of sodium metal was added and the solvent was distilled to dryness. The remaining white solid was heated in an oil bath at 130° C. for 1 hour, and 50 ml of xylene was added and refluxing was continued for 3 hours. The reaction mixture was cooled and filtered. The separate solid was dissolved in 30 ml of water, and the pH was adjusted to 5-6 and the aqueous solution was extracted with 2×300 ml of chloroform.

The chloroform extracts were collected, dried (anhydrous Na2SO4), filtered and evaporated in vacuo to afford a light green solid, mp 166°-169° C. of the title compound as the free base which was converted to the dihydrochloride salt, mp 232°-235° C.

Analysis for: $C_{24}H_{28}N_6O_2 2HCl$: Calculated: C, 57.02; H, 5.94; N, 16.63; Cl, 14.05: Found: C, 56.58; H, 6.01; N, 16.43; Cl, 13.57.

EXAMPLE 2

4,5-Dihydro-5-(phenylmethyl)-2-[4-[4-(2-pyrimidinyl)-1-piperazinyl]butyl]1H-pyrido[4,3-b]indole-1,3(2H)-dione The title compound was prepared following procedure of Example 1 with the exception that 3-carbethoxy-1-phenylmethylindole-2-acetic acid ethyl ester was used instead of 3-carbethoxy-1-methylindole-2-acetic acid ethyl ester and was converted to the dihydrochloride salt, mp 218°-220° C.

Analysis for: $C_{30}H_{32}N_6O_2 2HCl \cdot H_2O$: Calculated: C, 6.01; H, 6.0; N, 14.0: Found: C, 59.97; H, 5.71; N, 13.92.

EXAMPLE 3

2-[4-[4-(2-pyrimidinyl)-1-piperazinyl]butyl]pyrazino-[1,2-a]indole-1,3(2H,4H)-dione The title compound was prepared following procedure of Example 1 with the exception 1-carbmethoxymethyl-2-carbethoxyindole (Freed et al., U.S. Pat. No. 3,660,430) was used instead of 3-carbethoxy-1-methylindole-2-acetic acid ethyl ester and was converted to the dihydrochloride salt, mp 237°-239° C.

Analysis for: $C_{23}H_{26}N_6O_2 2HCl \cdot H_2O$: Calculated: C, 54.22; H, 5.89; N, 16.50: Found: C, 54.21; H, 5.82; N, 16.62.

What is claimed is:

1. A compound of the formula:

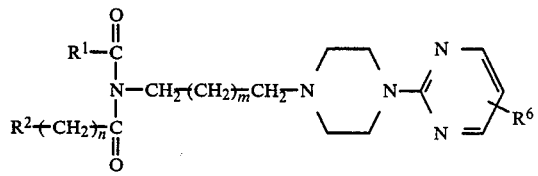

in which $R^1$ and $R^2$, taken together, represent an ortho-fused 1,2-indolo or 2,3-indolo moiety of the formulas:

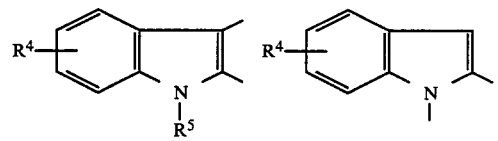

where $R^4$ is hydrogen, alkyl of 1 to 6 carbon atoms, alkoxy of 1 to 6 carbon atoms or halo;

$R^5$ is hydrogen, alkyl of 1 to 6 carbon atoms, benzyl, phenyl or substituted phenyl or benzyl where the substituent is taken from the group alkyl of 1 to 6 carbon atoms, alkoxy of 1 to 6 carbon atoms, halo or trifluoromethyl;

$R^6$ is alkyl of 1 to 6 carbon atoms, alkoxy of 1 to 6 carbon atoms or halo;

n is one of the integers 0 or 1; and m is one of the integers 0, 1, 2 or 3;

or a phamaceutically acceptable salt thereof.

2. A compound of the formula:

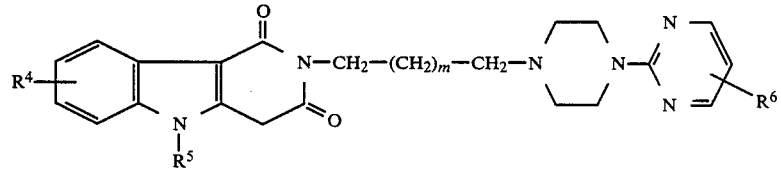

in which $R^4$ is hydrogen, alkyl of 1 to 6 carbon atoms, alkoxy of 1 to 6 carbon atoms or halo;

$R^5$ is hydrogen, alkyl of 1 to 6 carbon atoms, benzyl, phenyl or substituted phenyl or benzyl where the substituent is taken from the group alkyl of 1 to 6 carbon atoms, alkoxy of 1 to 6 carbon atoms, halo or trifluoromethyl;

$R^6$ is alkyl of 1 to 6 carbon atoms, alkoxy of 1 to 6 carbon atoms or halo; and m is one of the integers 0, 1, 2 or 3;

or a pharmaceutically acceptable salt thereof.

3. The compound of claim 2 which is 4,5-dihydro-5-methyl-2-[4-[4-(2-pyrimidinyl)-1-piperazinyl]butyl]1H-pyrido[4,3-b]indole-1,3(2H)-dione, or a pharmaceutically acceptable salt thereof.

4. The compound of claim 2 which is 4,5-dihydro-5-(phenylmethyl)-2-[4-[4-(2-pyrimidinyl)-1-piperazinyl]-butyl]1H-pyrido[4,3-b]indole-1,3(2H)-dione, or a pharmaceutically acceptable salt thereof.

5. The compound of claim 1 which is 2-[4-[4-(2-pyrimidinyl)-1-piperazinyl]butyl]pyrazino[1,2-a]indole-1,3(2H,4H)-dione, or a pharmaceutically acceptable salt thereof.

* * * * *